United States Patent [19]

Fischer et al.

[11] Patent Number: 4,824,864

[45] Date of Patent: Apr. 25, 1989

[54] STABILIZATION OF ZINEB

[75] Inventors: Roman Fischer; Knut Koob, both of Mutterstadt; Friedrich Loecher, Limburgerhof, all of Fed. Rep. of Germany

[73] Assignee: BASF Aktiengesellschaft, Ludwigshafen, Fed. Rep. of Germany

[21] Appl. No.: 754,012

[22] Filed: Jul. 11, 1985

[30] Foreign Application Priority Data

Jul. 14, 1984 [DE] Fed. Rep. of Germany ....... 3426078

[51] Int. Cl.$^4$ ...................... A01N 47/10; A01N 55/02
[52] U.S. Cl. ..................................... 514/494; 514/476; 514/970
[58] Field of Search ................................. 514/494, 970

[56] References Cited

U.S. PATENT DOCUMENTS

| 2,317,765 | 4/1973 | Hester | 167/22 |
| 2,992,161 | 7/1961 | Flenner | 514/494 |
| 3,278,373 | 10/1966 | Baker | 514/970 |
| 3,346,605 | 10/1967 | Windel | 260/429 |
| 4,107,300 | 8/1978 | Nakamura et al. | 424/200 |

FOREIGN PATENT DOCUMENTS

| 339666 | 11/1977 | Austria . |
| 1567068 | 4/1970 | Fed. Rep. of Germany . |
| 2445848 | 4/1975 | Fed. Rep. of Germany . |
| 1404865 | 5/1965 | France . |
| 2392605 | 12/1978 | France . |
| 0008209 | 1/1985 | Japan ................................. 514/970 |
| 1083115 | 9/1967 | United Kingdom . |

OTHER PUBLICATIONS

German Patent 1076434 Abstract 1960.
German Patent 1191170 Abstract 1965.
French Patent 1404865 Abstract 1965.
Chemical Abstracts 93:162283s 1980.
Chemical Abstracts 91:118670a 1979.
Chemical Abstracts 73:55004s (1970).
Chemical Abstracts 67:116083s 1967.
Chemical Abstracts 65:16769a 1966.
Chemical Abstracts 60:13815q 1964.

Primary Examiner—Allen J. Robinson
Attorney, Agent, or Firm—Keil & Weinkauf

[57] ABSTRACT

Zineb is stabilized by mixing it with calcium oxide in the absence of sulfur.

3 Claims, No Drawings

STABILIZATION OF ZINEB

The present invention relates to a process for the stabilization of zineb by mixing it with calcium oxide in the absence of sulfur.

It has been disclosed that zineb (zinc ethylenebisdithiocarbamate) can be used as a fungicide (U.S. Pat. No. 2,317,765). It has also been disclosed that the zineb/ammonia complex can be used as a fungicide (German Pat. No. 1,191,170). Hence, zineb is understood below as meaning both zinc ethylenebisdithiocarbamate and its complexes with ammonia, in which the amount of ammonia can vary.

The disadvantage of zineb is that it decomposes during storage, particularly at elevated temperatures.

It is an object of the present invention to prepare a zineb which decomposes only to a small extent, if at all. It has also been disclosed that zineb can be mixed with calcium hydroxide and sulfur (French Pat. No. 1,404,865). The mixture has the disadvantage that, owing to the admixing of the sulfur, the fungicidal action of zineb is altered in an undesirable manner where the fungicidal action required is that of zineb itself.

We have found that a zineb which is substantially stable to decomposition is obtained if calcium oxide is mixed with the zineb in the absence of sulfur. Calcium oxide is understood as meaning both calcium oxide as such (CaO) and calcium hydroxide (Ca(OH)$_2$). A good effect is achieved if from 1 to 15, in particular from 2 to 8, preferably 3, % by weight based on zineb, of calcium oxide is mixed with the zineb.

Mixing with less than 1% does not result in any significant improvement in the stability, while mixing with more than 15% results in excessive dilution of the zineb.

Example of the Preparation of a Mixture Containing 5% by Weight of CaO 1 mole of ethylenediamine is reacted with 2 moles of CS$_2$ and 2 moles of NH$_4$OH, and the resulting ammonium ethylenebisdithiocarbamate is precipitated as zineb using 1 mole of an aqueous ZnCl$_2$ solution. The precipitate is freed from the major part of the water, converted to a spray suspension by adding 20% (based on dry zineb) of surfactants, sprayed and dried. 5% by weight (based on dry zineb) of CaO are added to this dry product, and the components are mixed by means of a stirrer to give a homogeneous mixture.

If NH$_4$OH is used in an amount greater than that required for the reaction to give the ethylenebisdithiocarbamate, 1 or 2 moles of NH$_3$ are bound per mole of zineb, depending on the excess amount.

TEST PROCEDURE

Test Tube Storage Test

1. Principle

The product is introduced into test tubes and stored in both the open and tightly closed state at various temperatures, without regulation of the atmospheric humidity.

In this test procedure, it is possible only to determine the shelf life of the active ingredient at certain temperatures.

2. Procedure

The test tubes are filled to about 2 cm below the upper edge and stored in an oven at 50° C. Analyses (cleavable CS$_2$) are carried out at intervals of 1, 2, 4, 8 and 12 weeks.

3. Evaluation

The loss of active ingredient as a function of time can be tabulated and provides information about the storage behavior.

Beaker Storage Test

1. Principle

The samples (about 20 g) to be investigated are weighed into 250 ml beakers (diameter 6–6.5 cm), loaded with weights (25 g/cm$^2$) and exposed to various temperatures without regulation of atmospheric humidity. The physical properties of the formulations and the stability of the active ingredient are assessed.

2. Procedure 20 g of product are weighed into each beaker and, in the loaded state, are stored at room temperature, 40° C. and 50° C. Analyses are carried out after 4, 10, 20, 50, 60, 70 and 100 weeks.

3. Evaluation

The losses of active ingredient during the period of the storage test are used for assessing the storage behavior.

MIXTURES

A: 80 parts of weight of zineb.NH$_3$+10 parts of wetting agent+9 parts of kaolin+1 part of dispersant (no CaO)

Aa: 80 parts of zineb.NH$_3$+10 parts of wetting agent+7 parts of kaolin+1 part of dispersant+2 parts of CaO Ab: 80 parts of zineb.NH$_3$+10 parts of wetting agent+4 parts of kaolin+1 part of dispersant +5 parts of CaO Ac: 80 parts of zineb.NH$_3$+10 parts of wetting agent+1 part of dispersant30 9 parts of CaO (no kaolin)

C-Cc: as for A-Ac but using zineb.2NH$_3$ instead of zineb.NH$_3$

D-Dc: as for A-Ac but using zineb intead of zineb.NH$_3$

E: 82% by weight of zineb.NH$_3$+2% of wetting agent+2% of wetting agent+0.5% of dispersant +13.5% of kaolin F: 95% of mixture E+5% of CaO mixed dry.

SHELF LIFE—RESULTS

Storage at 50° C.
Test tube storage test

| Sample name | Initial amount of active ingredient | Amount of active ingredient after 4 weeks | 8 weeks | 12 weeks |
|---|---|---|---|---|
| A | 100 | 0 | — | — |
| Aa | 100 | 77 | 56 | 55 |
| Ab | 100 | 88 | 85 | 86 |
| Ac | 100 | 90 | 87 | 88 |
| C | 100 | 0 | — | — |
| Ca | 100 | 32 | 0 | — |
| Cb | 100 | 95 | 11 | 0 |
| Cc | 100 | 100 | 98 | 91 |
| D | 100 | 39 | 35 | 10 |
| Da | 100 | 64 | 62 | 15 |
| Db | 100 | 69 | 68 | 59 |
| Dc | 100 | 71 | 70 | 68 |

Beaker storage test with loading

| | Amount of active ingredient | | |
|---|---|---|---|
| | room temperature | 40° C. | 50° C. |

| E Storage time in weeks | | | |
|---|---|---|---|
| 4 | 100 | 100 | 80 |
| 10 | 100 | 15 | — |
| 20 | 100 | 3 | — |
| 50 | 90 | — | — |
| 60 | 80 | — | — |
| 70 | 80 | — | — |
| 100 | 75 | — | — |
| F Storage time in weeks | | | |
| 4 | 100 | 100 | 100 |
| 10 | 100 | 100 | 100 |
| 20 | 100 | 100 | 90 |
| 50 | 100 | 90 | 80 |
| 60 | 100 | 80 | 75 |
| 70 | 98 | 80 | 60 |
| 100 | 95 | 70 | 50 |

The use examples below illustrate the good fungicidal action of zineb stabilized according to the invention in comparison with conventional active ingredients. The formulations were applied in the form of an aqueous spray liquor prepared from the active ingredient, a wetting agent (adduct of ethylene oxide with nonylphenol) and water. 600 liters of spray liquor were used per hectare.

The following active ingredients were used for the use examples: coprecipitate of the ammonia complex of zinc, N,N'-ethylenebisdithiocarbamate and N,N'-polyethylenebisthiocarbamyl disulfide (metiram, DE-B-10 76 434), manganese ethylenebisdithiocarbamate (maneb, U.S. Pat. No. 2,504,404), manganese zinc ethylenebisdithiocarbamate (mancozeb, U.S. Pat. No. 3,379,610), and a mixture of zineb and 5% by weight of calcium oxide (according to the invention, A, prepared according to the preparation example).

USE EXAMPLE 1

Controlling *Venturia inaequalis* in Apples (Golden Delicious Variety) in Field Trial

| Agent | Application rate kg/ha | Time of treatment + | Rust on fruit, % in various classes for infestation at harvesting | | | |
|---|---|---|---|---|---|---|
| | | | none | slight | moderate | pronounced |
| untreated | — | — | 56.0 | 39.5 | 4.2 | 0.3 |
| metiram | 3.0/ 2.25 | I/II + III ⊕ ⊕⊕ | 74.8 | 25.0 | 0.2 | 0 |
| mancozeb | 3.0/ 2.25 | " | 69.0 | 29.7 | 1.3 | 0 |
| A | 3.0/ 2.25 | " | 77.0 | 22.5 | 0.5 | 0 |

Comments:
+ 1 l sprays
⊕ phase I: pre-blossom, application rate 2.25 kg/ha of active ingredient
⊕⊕ phases II + III: blossom + post-blossom to end of shooting, application rate 3 kg/ha of active ingredient

USE EXAMPLE 2

Control of *Plasmopara viticola* in Grapes (Grenache Variety) in Field Trial

| Agent | Concentration of the active ingredient in the spray liquor, in % by weight | Infestation in % |
|---|---|---|
| untreated | — | 72.7 |
| metiram | 0.4 | 10.2 |
| mancozeb | 0.35 | 10.4 |
| A | 0.4 | 7.5 |
| A | 0.35 | 9.5 |

USE EXAMPLE 3

Control of *Phytophthora infestans* in Potatoes in Field Trial

| Agent | Concentration of active ingredient in the spray liquor, in % by weight | Phytophthora infestans, infestation in % |
|---|---|---|
| untreated | — | 58.75 |
| maneb | 1.8 | 23.75 |
| metiram | 1.8 | 21.25 |
| A | 1.8 | 17.50 |

USE EXAMPLE 4

Control of *Alternaria solani* in Tomatoes (Floradale Variety) in Field Trial

| Agent | Concentration of active ingredient in the spray liquor, in % by weight | Alternaria solani infestation in % |
|---|---|---|
| untreated | — | 25.1 |
| metiram | 0.2 | 12.2 |
| maneb | 0.2 | 14.1 |
| A | 0.2 | 10.8 |

Comments: application rate 1000 l/ha of spray liquor

We claim:
1. A method of stabilizing fungicidal compositions consisting essentially essential of zineb to reduce substantially the decomposition of zineb during storage, which method consists of mixing into said composition from 1 to 15% by weight of calcium oxide based on the weight of zineb in the composition to produce a homogeneous mixture.

2. The method of claim 1, wherein the amount of calcium oxide mixed into the composition is from 2 to 8% by weight based on the weight of zineb in the composition.

3. The method of claim 1, wherein the amount of calcium oxide mixed into the composition is about 3% based on the weight of zineb in the composition.

* * * * *

UNITED STATES PATENT AND TRADEMARK OFFICE
CERTIFICATE OF CORRECTION

PATENT NO. : 4,824,864

DATED : April 25, 1989

INVENTOR(S) : Fischer et al

It is certified that error appears in the above-identified patent and that said Letters Patent is hereby corrected as shown below:

Claim 1, line 2, "consisting essentially essential of zineb" should read -- consisting essentially of zineb --.

Signed and Sealed this

Second Day of January, 1990

Attest:

JEFFREY M. SAMUELS

Attesting Officer        Acting Commissioner of Patents and Trademarks